US008335318B2

(12) United States Patent
Pan

(10) Patent No.: US 8,335,318 B2

(45) Date of Patent: Dec. 18, 2012

(54) ACTIVE NOISE REDUCTION ADAPTIVE FILTERING

(75) Inventor: Davis Y. Pan, Arlington, MA (US)

(73) Assignee: Bose Corporation, Framingham, MA (US)

( * ) Notice: Subject to any disclaimer, the term of this patent is extended or adjusted under 35 U.S.C. 154(b) by 693 days.

(21) Appl. No.: 12/408,441

(22) Filed: Mar. 20, 2009

(65) Prior Publication Data

US 2010/0239105 A1 Sep. 23, 2010

(51) Int. Cl.

| | |
|---|---|
| ***H04R 29/00*** | (2006.01) |
| ***H03G 3/20*** | (2006.01) |
| ***A61F 11/06*** | (2006.01) |
| ***G10K 11/16*** | (2006.01) |
| ***H03B 29/00*** | (2006.01) |
| ***H04B 1/00*** | (2006.01) |
| ***H04B 15/00*** | (2006.01) |

(52) U.S. Cl. .......... 381/56; 381/57; 381/71.2; 381/71.3; 381/71.4; 381/86; 381/94.9

(58) Field of Classification Search ................. 381/94.8, 381/71.14, 94.9, 94.2, 94.3, 94.7, 71.4, 71.2, 381/98–103, 56, 57, 71.1, 71.3, 91.4, 86
See application file for complete search history.

(56) References Cited

U.S. PATENT DOCUMENTS

| | | | | |
|---|---|---|---|---|
| 3,803,357 | A * | 4/1974 | Sacks | 381/94.8 |
| 5,499,302 | A | 3/1996 | Nagami et al. | |
| 5,649,018 | A | 7/1997 | Gifford et al. | |
| 6,118,878 | A | 9/2000 | Jones | |
| 6,963,649 | B2 * | 11/2005 | Vaudrey et al. | 381/94.7 |
| 7,885,417 | B2 * | 2/2011 | Christoph | 381/71.11 |
| 2004/0240677 | A1 | 12/2004 | Onishi et al. | |
| 2007/0297619 | A1 * | 12/2007 | Pan | 381/71.11 |
| 2008/0159553 | A1 | 7/2008 | Copley et al. | |

FOREIGN PATENT DOCUMENTS

WO 2008002873 A2 1/2008

OTHER PUBLICATIONS

International Search Report and Written Opinion dated Jan. 27, 2011 for PCT/US10/023529.

* cited by examiner

*Primary Examiner* — Phat X Cao
*Assistant Examiner* — Diana C Vieira

(57) ABSTRACT

An active noise reduction system that reduces the incidence of divergence in the presence of high amplitude interfering noise. A limited frequency range threshold is established.

27 Claims, 6 Drawing Sheets

ACTIVE NOISE REDUCTION ADAPTIVE FILTERING

BACKGROUND

This specification describes an active noise reduction system and more particularly an active noise reduction system that reduces divergence of adaptive filters in the presence of high amplitude interfering noise.

SUMMARY

In one aspect an apparatus includes a feed forward active noise reduction system including a transducer for transducing acoustic noise at a location to a noise signal; circuitry for determining the amplitude of the noise signal in a broadband frequency range; circuitry for comparing the amplitude of the noise signal in the broadband frequency range with a broadband threshold; circuitry for determining the amplitude of the noise signal over a limited portion of the broadband frequency range; circuitry for comparing the amplitude of the noise signal in the limited portion of the broadband frequency range with a limited frequency range threshold; and circuitry for modifying the noise signal if the amplitude of the noise signal in the broadband frequency range exceeds the broadband threshold or the amplitude of the noise signal in the limited portion of broadband frequency range exceeds the limited frequency range threshold. The circuitry for modifying the noise signal may include circuitry for modifying a gain applied to the noise signal. The active noise reduction system may further include a low pass filter for filtering the noise signal to provide a low pass filtered noise signal and circuitry for providing the low pass filtered noise signal to the circuitry for comparing the noise signal in the limited portion of the broadband frequency range. The active noise reduction may further include a band pass filter for filtering the noise signal to provide a band pass filtered noise signal and circuitry for providing the band pass filtered noise signal to the circuitry for comparing the noise signal in the limited portion of the broadband frequency range. The active noise reduction system may be for reducing acoustic noise in a vehicle cabin. The broadband threshold may be different than the limited frequency range threshold.

In another aspect, an apparatus includes a feed forward active noise reduction system including a vehicle cabin; a transducer for transducing acoustic noise in the vehicle cabin to a noise signal; circuitry for determining the amplitude of the noise signal in a limited portion of the frequency range; circuitry for comparing the amplitude of the noise signal in the limited portion of the frequency range with a limited frequency range threshold; and circuitry for modifying the noise signal if the amplitude of the noise signal in the limited portion of the frequency range exceeds the limited frequency range threshold. The active noise reduction system may further include circuitry for determining the amplitude of the noise signal over a broadband frequency range; circuitry for comparing the amplitude of the noise signal in the broadband frequency range with a broadband threshold; and circuitry for modifying the noise signal if the amplitude of the noise signal in the limited portion of the frequency range exceeds the limited frequency range threshold or the amplitude of the noise signal in the broadband frequency range exceeds the broadband threshold. The broadband frequency range threshold may be different than the limited frequency range threshold. The circuitry for modifying the noise signal may include circuitry for modifying a gain applied to the noise signal. The active noise reduction system may further include a low pass filter for filtering the noise signal to provide a low pass filtered noise signal and circuitry for providing the low pass filtered noise signal to the circuitry for comparing the noise signal in the limited portion of the frequency range. The active noise reduction system may further include a band pass filter for filtering the noise signal to provide a band pass filtered noise signal and circuitry for providing the band pass filtered noise signal to the circuitry for comparing the noise signal in the limited portion of the frequency range.

In another aspect, a method for operating a feed forward active noise reduction system for reducing noise includes detecting acoustic energy at a location; transducing the acoustic noise to a noise signal; determining the amplitude of the noise signal in a broadband frequency range; comparing the amplitude of the noise signal in the broadband frequency range with a broadband threshold; determining the amplitude of the noise signal over a limited portion of the broadband frequency range; comparing the amplitude of the noise signal in the limited portion of the broadband frequency range with a limited frequency range threshold; and if the amplitude of the noise signal in the broadband frequency range exceeds the broadband threshold or the amplitude of the noise signal in the limited portion of the broadband frequency range exceeds the limited frequency range threshold, modifying the noise signal. The modifying the noise signal may include modifying a gain applied to the noise signal. The method for operating an active noise reduction may further include low pass filtering the noise signal prior to the comparing the noise signal in the limited portion of the broadband frequency range. The method for operating an active noise reduction system may further include band pass filtering the noise signal prior to the comparing the noise signal in the limited portion of the broadband frequency range. The location may be in a vehicle cabin. The broadband threshold may be different than the limited frequency range threshold.

In another aspect, a method for operating a feed forward active noise reduction system includes transducing acoustic noise in a vehicle cabin to a noise signal; determining the amplitude of the noise signal in a limited portion of the frequency range; comparing the amplitude of the noise signal in the limited portion of the frequency range with a limited frequency range threshold; and if the amplitude of the noise signal in the limited portion of the frequency range exceeds the limited frequency range threshold, modifying the noise signal. The method for operating an active noise reduction system may further include determining the amplitude of the noise signal over a broadband frequency range; comparing the amplitude of the noise signal in the broadband frequency range with a broadband threshold; and if the amplitude of the noise signal in the limited portion of the frequency range exceeds the limited frequency range threshold or the amplitude of the noise signal in the broadband frequency range exceeds the broadband threshold, modifying the noise signal. The modifying the noise signal may include modifying a gain applied to the noise signal. The method for operating an active noise reduction system may further includes low pass filtering the noise signal prior to the comparing the noise signal in the limited portion of the frequency range. The method for operating an active noise reduction system may further include band pass filtering the noise signal prior to the comparing the noise signal in the limited portion of the frequency range. The limited frequency range threshold may be different than the broadband threshold.

Other features, objects, and advantages will become apparent from the following detailed description, when read in connection with the following drawing, in which:

DETAILED DESCRIPTION

Figure 1A:
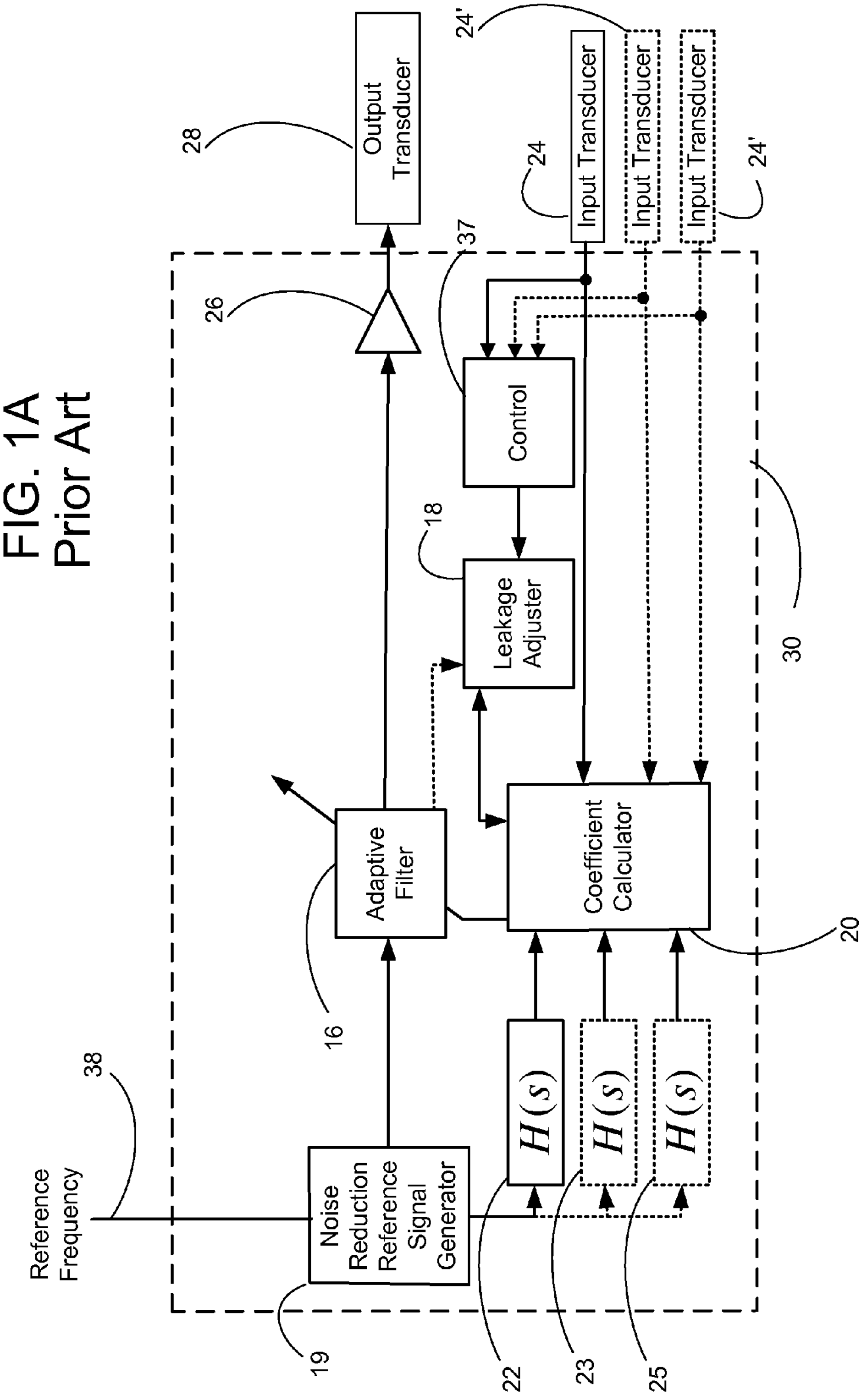
FIG. 1A Prior Art
FIGS. 1A and 1B are block diagrams of active noise reduction systems.

Though the elements of several views of the drawing may be shown and described as discrete elements in a block diagram and may be referred to as "circuitry", unless otherwise indicated, the elements may be implemented as one of, or a combination of, analog circuitry, digital circuitry, or one or more microprocessors executing software instructions. The software instructions may include digital signal processing (DSP) instructions. Unless otherwise indicated, signal lines may be implemented as discrete analog or digital signal lines. Multiple signal lines may be implemented as one discrete digital signal line with appropriate signal processing to process separate streams of audio signals, or as elements of a wireless communication system. Some of the processing operations may be expressed in terms of the calculation and application of coefficients. The equivalent of calculating and applying coefficients can be performed by other analog or DSP techniques and are included within the scope of this patent application. Unless otherwise indicated, audio signals may be encoded in either digital or analog form; conventional digital-to-analog and analog-to-digital converters may not be shown in circuit diagrams. This specification describes an active noise reduction system. Active noise reduction systems are typically intended to eliminate undesired noise (i.e. the goal is zero noise). However in actual noise reduction systems undesired noise is attenuated, but complete noise reduction is not attained. In this specification "driving toward zero" means that the goal of the active noise reduction system is zero noise, though it is recognized that actual result is significant attenuation, not complete elimination.

Referring to FIG. 1A, there is shown a block diagram of a feed forward active noise reduction system. Communication path 38 is coupled to noise reduction reference signal generator 19 for presenting to the noise reduction reference signal generator a reference frequency. The noise reduction reference signal generator is coupled to filter 22 and adaptive filter 16. The filter 22 is coupled to coefficient calculator 20. Input transducer 24 is coupled to control block 37 and to coefficient calculator 20, which is in turn bidirectionally coupled to leakage adjuster 18 and adaptive filter 16. Adaptive filter 16 is coupled to output transducer 28 by power amplifier 26. Control block 37 is coupled to leakage adjuster 18. Optionally, there may be additional input transducers 24' coupled to coefficient calculator 20, and optionally, the adaptive filter 16 may be coupled to leakage adjuster 18. If there are additional input transducers 24', there typically will be a corresponding filter 23, 25.

In operation, a reference frequency, or information from which a reference frequency can be derived, is provided to the noise reduction reference signal generator 19. The noise reduction reference signal generator generates a noise reduction signal, which may be in the form of a periodic signal, such as a sinusoid having a frequency component related to the engine speed, to filter 22 and to adaptive filter 16. Input transducer 24 detects periodic vibrational energy having a frequency component related to the reference frequency and transduces the vibrational energy to a noise signal (sometimes referred to as "error signal", for convenience hereinafter referred to as a noise signal), which is provided to coefficient calculator 20. Coefficient calculator 20 determines coefficients for adaptive filter 16. Adaptive filter 16 uses the coefficients from coefficient calculator 20 to modify the amplitude and/or phase of the noise cancellation reference signal from noise reduction reference signal generator 19 and provides the modified noise cancellation signal to power amplifier 26. The noise reduction signal is amplified by power amplifier 26 and transduced to vibrational energy by output transducer 28. Control block 37 controls the operation of the active noise reduction elements, for example by activating or deactivating the active noise reduction system or by adjusting the amount of noise attenuation.

The adaptive filter 16, the leakage adjuster 18, and the coefficient calculator 20 operate repetitively and recursively to provide a stream of filter coefficients that cause the adaptive filter 16 to modify a signal that, when transduced to periodic vibrational energy, attenuates the vibrational energy detected by input transducer 24. Filter 22, which can be characterized by transfer function H(s), compensates for effects on the energy transduced by input transducer 24 of components of the active noise reduction system (including power amplifier 26 and output transducer 28) and of the environment in which the system operates.

Input transducer(s) 24, 24' may be one of many types of devices that transduce vibrational energy to electrically or digitally encoded signals, such as an accelerometer, a microphone, a piezoelectric device, and others. If there is more than one input transducer, 24, 24', the filtered inputs from the transducers may be combined in some manner, such as by averaging, or the input from one may be weighted more heavily than the others. Filter 22, coefficient calculator 20, leakage adjuster 18, and control block 37 may be implemented as instructions executed by a microprocessor, such as a DSP device. Output transducer 28 can be one of many electromechanical or electroacoustical devices that provide periodic vibrational energy, such as a motor or an acoustic driver.

Figure 1B:
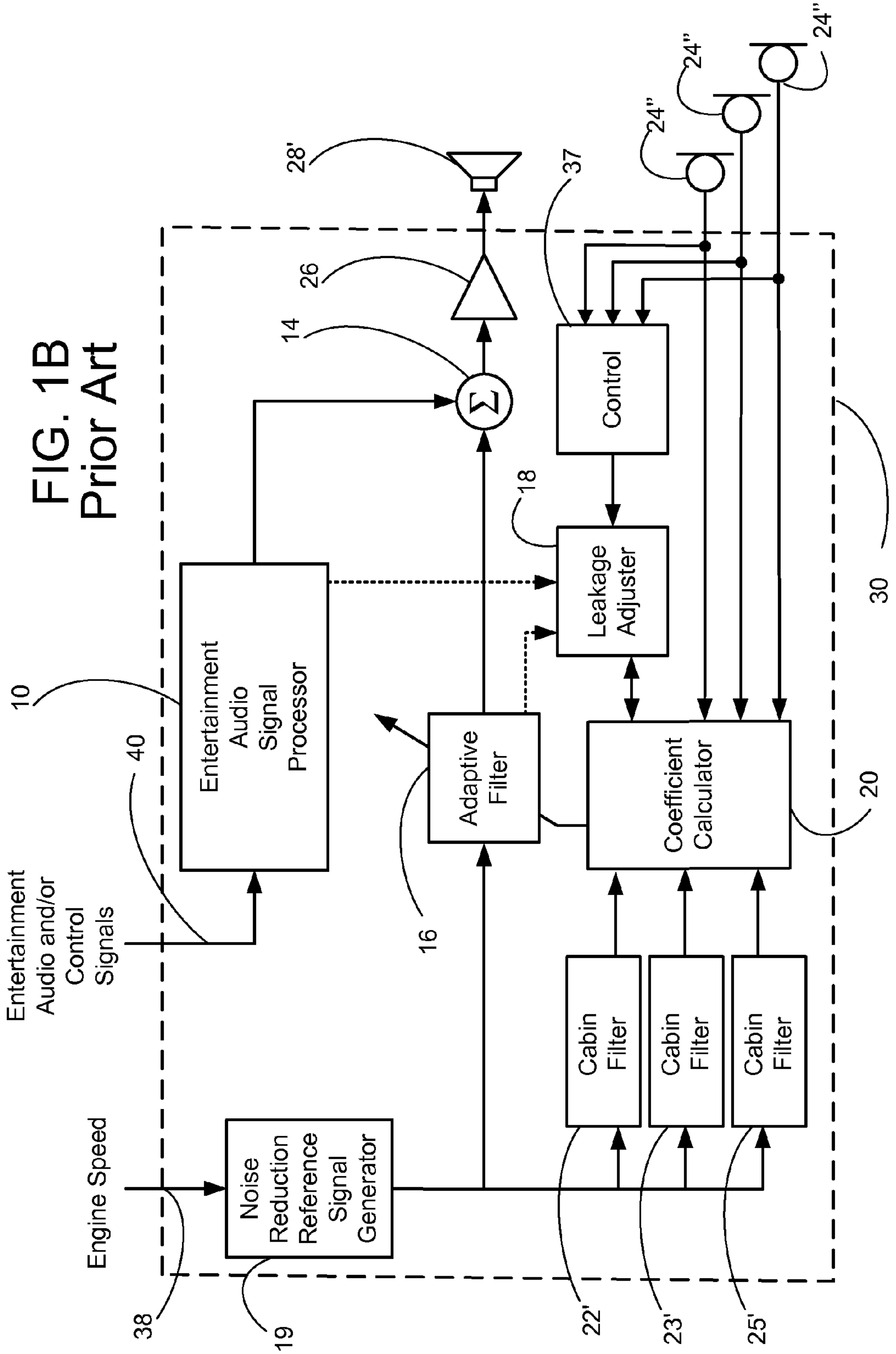
FIG. 1B Prior Art

Referring to FIG. 1B, there is shown a block diagram including elements of the feed forward active noise reduction system of FIG. 1A. The feed forward active noise reduction system of FIG. 1B is implemented as an active acoustic noise reduction system in a vehicle cabin, but also may be configured for use in other enclosed spaces, such as a room or control station, or for use in unenclosed spaces, such as a convertible with the top down, a vehicle with the windows open, or a machine operating in an unenclosed space. The system of FIG. 1B also includes elements of an audio entertainment or communications system. For example, if the system of FIG. 1B is implemented in a cabin in a vehicle, such as a passenger car, van, truck, sport utility vehicle, construction or farm vehicle, military vehicle, or airplane, the audio entertainment or communications system may be associated with the vehicle. Entertainment audio signal processor 10 is operationally coupled to signal line 40 to receive an entertainment audio signal and/or an entertainment system control signal, and is coupled to combiner 14 and may be coupled to leakage adjuster 18. Noise reduction reference signal generator 19 is operationally coupled to signal line 38 and to adaptive filter 16 and cabin filter 22', which corresponds to the filter 22 of FIG. 1A. Adaptive filter 16 is coupled to combiner 14, to coefficient calculator 20, and optionally may be directly coupled to leakage adjuster 18. Coefficient calculator 20 is coupled to cabin filter 22', to leakage adjuster 18, and to microphones 24", which correspond to the input transducers 24, 24' of FIG. 1A. Combiner 14 is coupled to power amplifier 26 which is coupled to acoustic driver 28', which corresponds to output transducer 28 of FIG. 1A. Control block 37 is operationally coupled to leakage adjuster 18 and to microphones 24". In many vehicles, entertainment audio signal processor 10 is coupled to a plurality of combiners 14, each of which is coupled to a power amplifier 26 and an acoustic driver 28'.

Each of the plurality of combiners 14, power amplifiers 26, and acoustic drivers 28' may be coupled, through elements such as amplifiers and combiners to one of a plurality of adaptive filters 16, each of which has associated with it a leakage adjuster 18, a coefficient calculator 20, and a cabin filter 22. A single adaptive filter 16, associated leakage adjuster 18, and coefficient calculator 20 may modify noise cancellation signals presented to more than one acoustic driver. For simplicity, only one combiner 14, one power amplifier 26, and one acoustic driver 28' are shown. Each microphone 24" may be coupled to more than one coefficient calculator 20.

All or some of the entertainment audio signal processor 10, the noise reduction reference signal generator 19, the adaptive filter 16, the cabin filter 22', the coefficient calculator 20 the leakage adjuster 18, the control block 37, and the combiner 14 may be implemented as software instructions executed by one or more microprocessors or DSP chips. The power amplifier 26 and the microprocessor or DSP chip may be components of an amplifier 30.

In operation, some of the elements of FIG. 1B operate to provide audio entertainment and audibly presented information (such as navigation instructions, audible warning indicators, cellular phone transmission, operational information [for example, low fuel indication], and the like) to occupants of the vehicle. An entertainment audio signal from signal line 40 is processed by entertainment audio signal processor 10. A processed audio signal is combined with an active noise reduction signal (to be described later) at combiner 14. The combined signal is amplified by power amplifier 26 and transduced to acoustic energy by acoustic driver 28'.

Some elements of the device of FIG. 1B operate to actively reduce noise in the vehicle compartment caused by the vehicle engine and other noise sources. The engine speed, which is typically represented as pulses indicative of the rotational speed of the engine, also referred to as revolutions per minute or RPM, is provided to noise reduction reference signal generator 19, which determines a reference frequency according to $$f(\text{Hz}) = \frac{\text{engine\_speed}(rpm)}{60}.$$

A signal related to the reference frequency is provided to cabin filter 22'. The noise reduction reference signal generator 19 generates a noise cancellation signal, which may be in the form of a periodic signal, such as a sinusoid having a frequency component related to a harmonic of the engine speed. The noise cancellation signal is provided to adaptive filter 16 and in parallel to cabin filter 22'. Microphone 24" transduces acoustic energy, which may include acoustic energy corresponding to entertainment audio signals, in the vehicle cabin to a noise audio signal, which is provided to the coefficient calculator 20. The coefficient calculator 20 modifies the coefficients of adaptive filter 16. Adaptive filter 16 uses the coefficients to modify the amplitude and/or phase of the noise cancellation signal from noise reduction reference signal generator 19 and provides the modified noise cancellation signal to signal combiner 14. The combined effect of some electroacoustic elements (for example, acoustic driver 28', power amplifier 26, microphone 24" and of the environment within which the noise reduction system operates) can be characterized by a transfer function H(s). Cabin filter 22' models and compensates for the transfer function H(s). The operation of the leakage adjuster 18 and control block 37 will be described below.

The adaptive filter 16, the leakage adjuster 18, and the coefficient calculator 20 operate repetitively and recursively to provide a stream of filter coefficients that cause the adaptive filter 16 to modify an audio signal that, when radiated by the acoustic driver 28', drives the magnitude of specific spectral components of the signal detected by microphone 24" to some desired value. The specific spectral components typically correspond to fixed multiples of the frequency derived from the engine speed. The specific desired value to which the magnitude of the specific spectral components is to be driven may be zero, but may be some other value as will be described below.

The elements of FIGS. 1A and 1B may also be replicated and used to generate and modify noise reduction signals for more than one frequency. The noise reduction signal for the other frequencies is generated and modified in the same manner as described above.

The content of the audio signals from the entertainment audio signal source includes conventional audio entertainment, such as for example, music, talk radio, news and sports broadcasts, audio associated with multimedia entertainment and the like, and, as stated above, may include forms of audible information such as navigation instructions, audio transmissions from a cellular telephone network, warning signals associated with operation of the vehicle, and operational information about the vehicle. The entertainment audio signal processor may include stereo and/or multi-channel audio processing circuitry. Adaptive filter 16 and coefficient calculator 20 together may be implemented as one of a number of filter types, such as an n-tap delay line; a Leguerre filter; a finite impulse response (FIR) filter; and others. The adaptive filter may use one of a number of types of adaptation schemes, such as a least mean squares (LMS) adaptive scheme; a normalized LMS scheme; a block LMS scheme; or a block discrete Fourier transform scheme; and others. The combiner 14 is not necessarily a physical element, but rather may be implemented as a summation of signals.

Though shown as a single element, the adaptive filter 16 may include more than one filter element. In some embodiments of the system of FIG. 1B, adaptive filter 16 includes two FIR filter elements, one each for a sine function and a cosine function with both sinusoid inputs at the same frequency, each FIR filter using an LMS adaptive scheme with a single tap, and a sample rate which may be related to the audio frequency sampling rate r (for example $$\frac{r}{28}).$$

Suitable adaptive algorithms for use by the coefficient calculator 20 may be found in *Adaptive Filter Theory,* 4*th* *Edition* by Simon Haykin, ISBN 0130901261.

Many active noise reduction systems in vehicles are designed to attenuate engine noise at the reference frequency. Sometimes events (for example driving over a large bump) or conditions (for example an open window) not related to the engine may result in high amplitude, interfering noise with high amounts of acoustic energy at the reference frequency. The high amplitude interfering noise may be non-correlated or broadband or both, and is typically the result of some event or condition not associated with the operation of the engine. The portion of the noise signal detected by input transducer 24 or 24' resulting from an event or condition resulting in high amplitude interfering noise may be as much or even greater than the portion of the noise signal caused by the engine. This may cause the adaptive system to diverge, resulting in undesirable audible artifacts.

Figure 2:
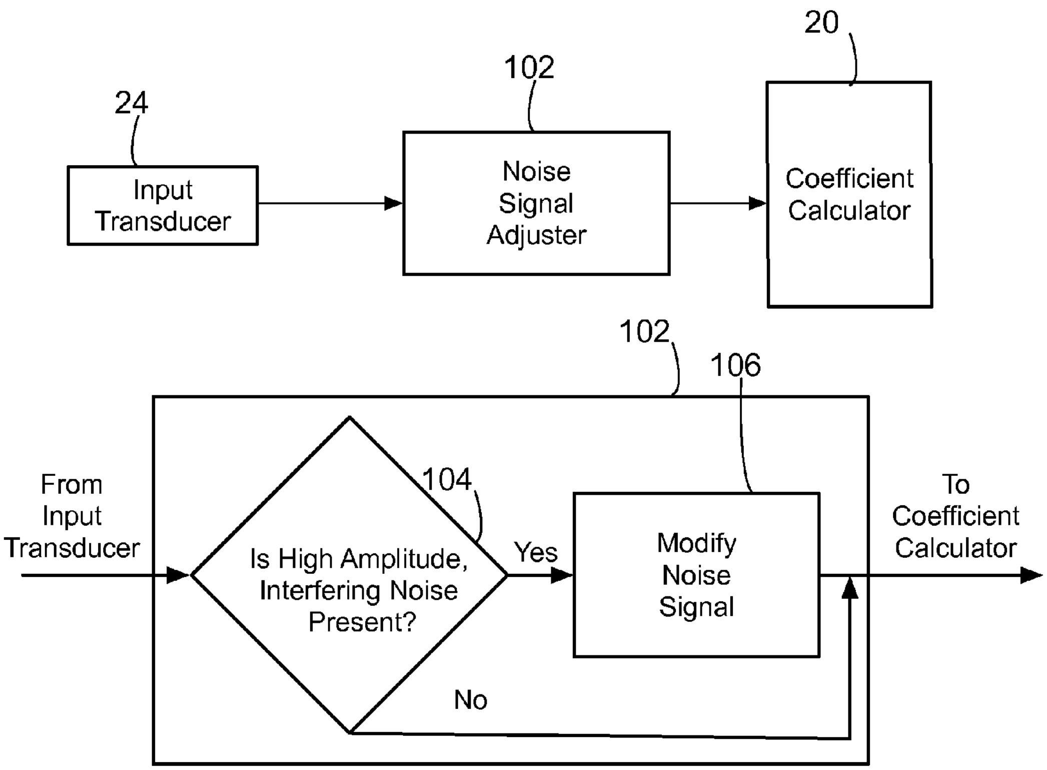
FIG. 2 is a block diagram of the operation of a portion of an active noise reduction system.

FIG. 2 shows a block diagram of the operation of an active noise reduction system to prevent system divergence resulting from high amplitude interfering noise with acoustic energy at the reference frequency. The input transducer 24 (of FIG. 1A or 24' of FIG. 1B) is coupled to the coefficient calculator 20 by noise signal adjuster 102. (The input transducer 24 and the coefficient calculator 20 are spatially reversed in FIGS. 1A/1B and FIG. 2; the logical arrangement however is the same in FIGS. 1A/B and FIG. 2).

In operation, the noise signal adjuster 102 receives the noise or error signal from the input transducer 24 and at block 104 determines if high amplitude interfering noise is present in the noise signal. If high amplitude interfering noise is present, at block 106, the noise signal is modified in a manner such that the adaptive system does not diverge, and the noise signal is presented to the coefficient calculator. If at step 104, high amplitude interfering noise is not present, the noise signal is presented to the coefficient calculator so that the active noise reduction system functions normally.

In one embodiment, blocks 102, 104, and 106 are performed by DSP's executing software instructions and the modifying the noise signal at block 106 includes modifying the gain applied to the noise signal, which could include setting the gain to unity (so that the signal is neither amplified nor attenuated) or setting the gain to zero (so that the noise signal is set to zero).

Figure 3:
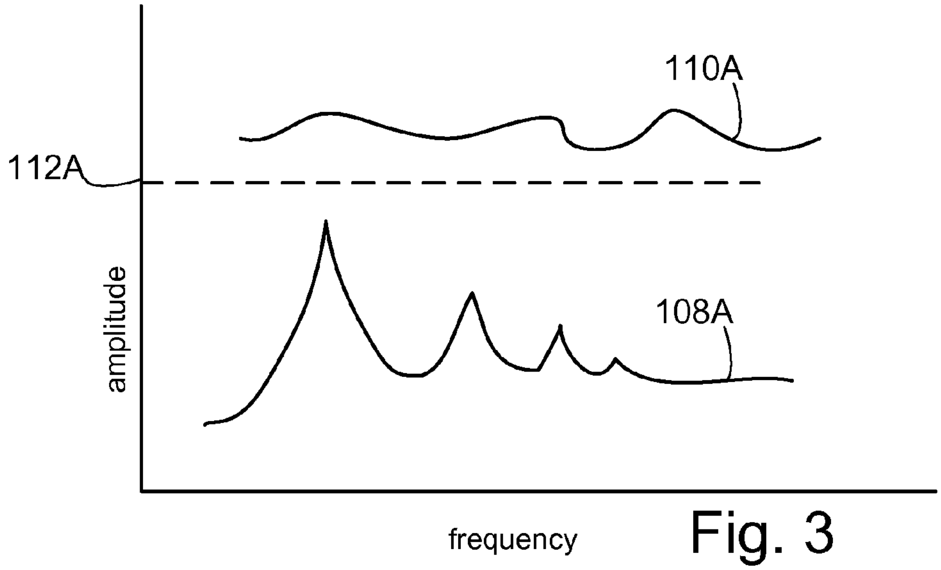
FIGS. 3-7 are plots of amplitude vs. frequency.

One method of determining if there is high amplitude interfering noise present is to measure the wide band amplitude of the noise signal and determine if the wide band amplitude is above a threshold. This method is illustrated in FIG. 3. Curve 108A represents the highest expected amplitude of engine noise by frequency. The highest expected amplitude curve may be determined empirically. Engine noise is typically narrowband at known harmonics of the reference frequency. Curve 110A represents the noise signal. Curve 112A represents the threshold amplitude. If the amplitude of the noise signal is above the threshold 112A, it is determined that high amplitude interfering noise is present. If the amplitude of the noise signal is below the threshold amplitude, it is determined that high amplitude interfering noise is not present.

Figure 4:
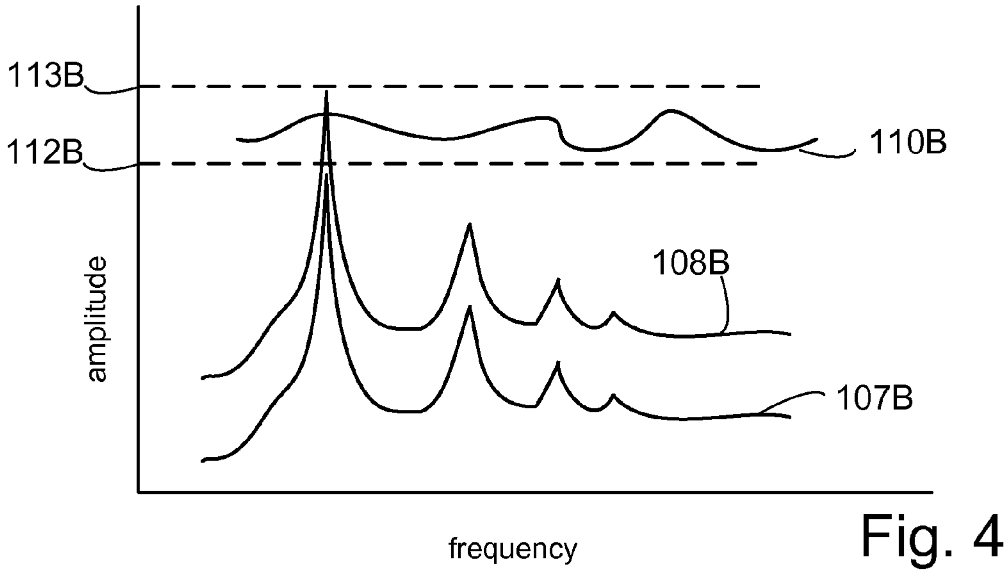

In some circumstances, however, setting a threshold amplitude may be difficult. For example in FIG. 4, if the highest expected amplitude curve of the engine noise (represented by curve 108B) has a peak value that is high relative to the noise signal (represented by curve 110B), it may be difficult to set a threshold that accurately determines if high amplitude interfering noise is present or not. If the threshold is set at level 112B, which is appropriate for a typical engine noise curve represented by curve 107B, it may be determined that high amplitude interfering noise is present even if it is not. If the threshold is set at level 113B, which is appropriate for the highest expected amplitude curve 108B, it may be determined that high amplitude interfering noise is not present, even if it is.

Figure 5:
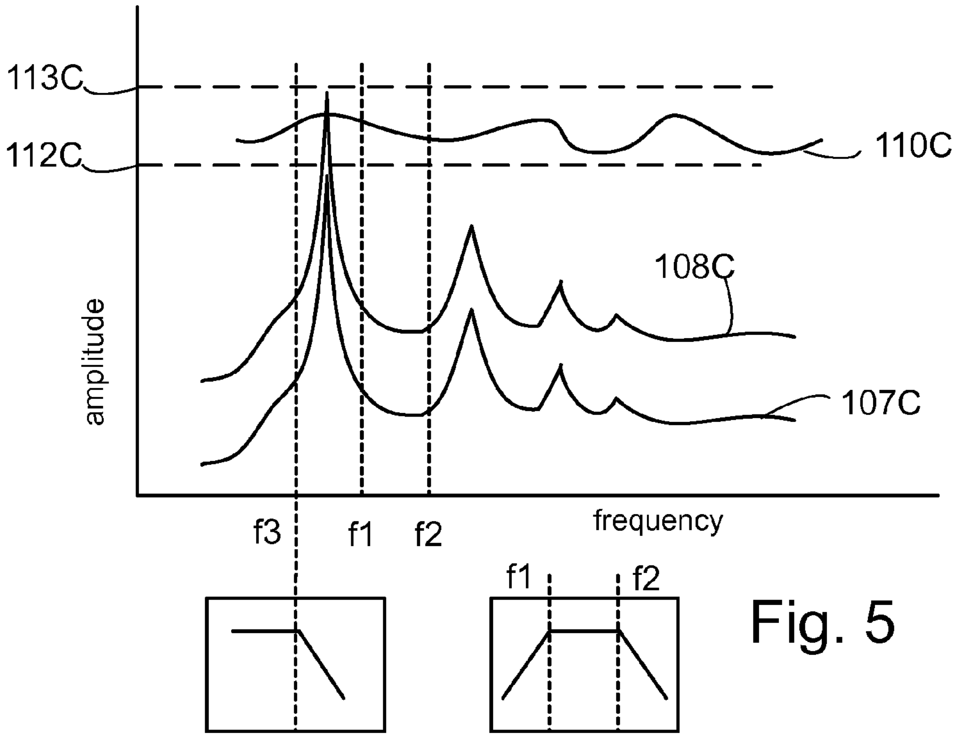

FIG. 5 illustrates a method of determining if high amplitude interfering noise is present that can be used in a situation in which the highest amplitude of the engine noise (represented in FIG. 5 by curve 108C) is nearly as great as, or greater than, the amplitude of the interfering noise. The method of FIG. 5 is most effective if the interfering noise (represented by curve 110C) is relatively narrowband or has high amplitude at frequencies between the peak amplitudes of the engine noise, or below the first peak of the engine noise, or both. The noise signal is band pass filtered with a pass band between frequencies f1 and f2, between amplitude peaks of the engine noise, or low pass filtered with a break frequency f3, below the first amplitude peak of the engine noise. The amplitude of the band limited noise is compared to a frequency band threshold 112C that can be lower than broadband threshold 113C, which can be the same as the broadband threshold 113B of FIG. 4, and even lower than the peak amplitude of the engine noise. If the amplitude is above the frequency band threshold, it is determined that high amplitude interfering noise is present. Typically, the low pass filter method is easier to implement than the band pass filter method. With the band pass method, because the frequencies at which the peaks occur may vary with conditions, such as engine speed, the frequencies f1 and f2 between the peaks must vary also. While the explanation above employs low pass or band pass filters, other methods of detecting band-limited energy, for example fast Fourier transforms (FFT's) or least mean squares (LMS) filters may also be used.

Figure 6:
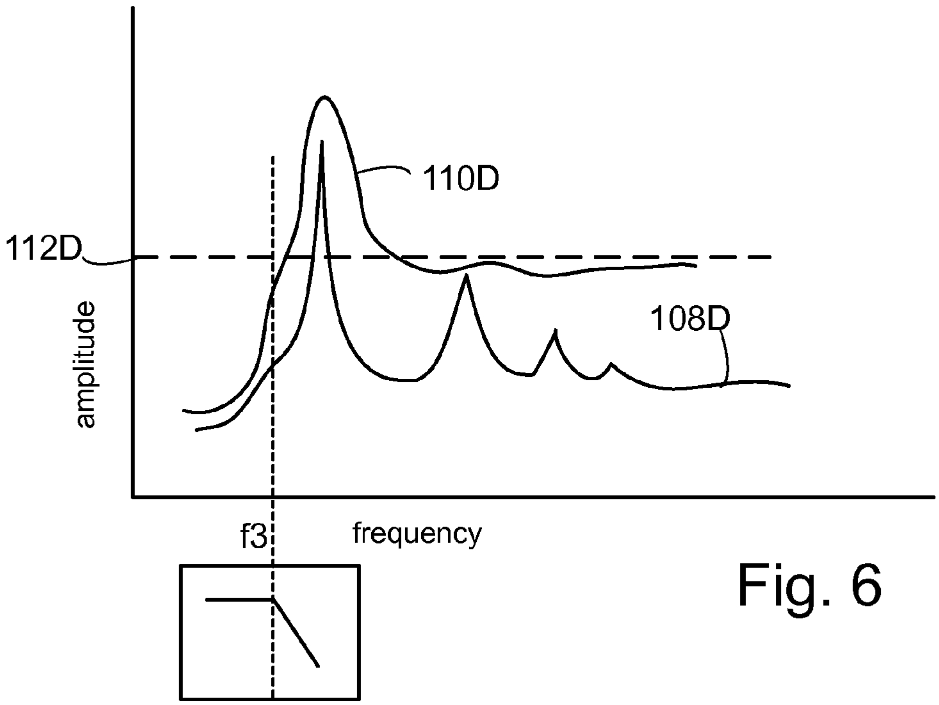

In the situation of FIG. 6, the engine noise curve 108D is similar to the engine noise 108C of FIG. 5. However the high amplitude, interfering noise 110D does not have a high level of acoustic energy below frequency f3 but does have a high level of acoustic energy at the frequency of the highest expected amplitude of the engine noise. If the method of FIG. 5 is applied to the situation of FIG. 6, it may be determined that high amplitude interfering noise is not present, even though it is.

Figure 7:
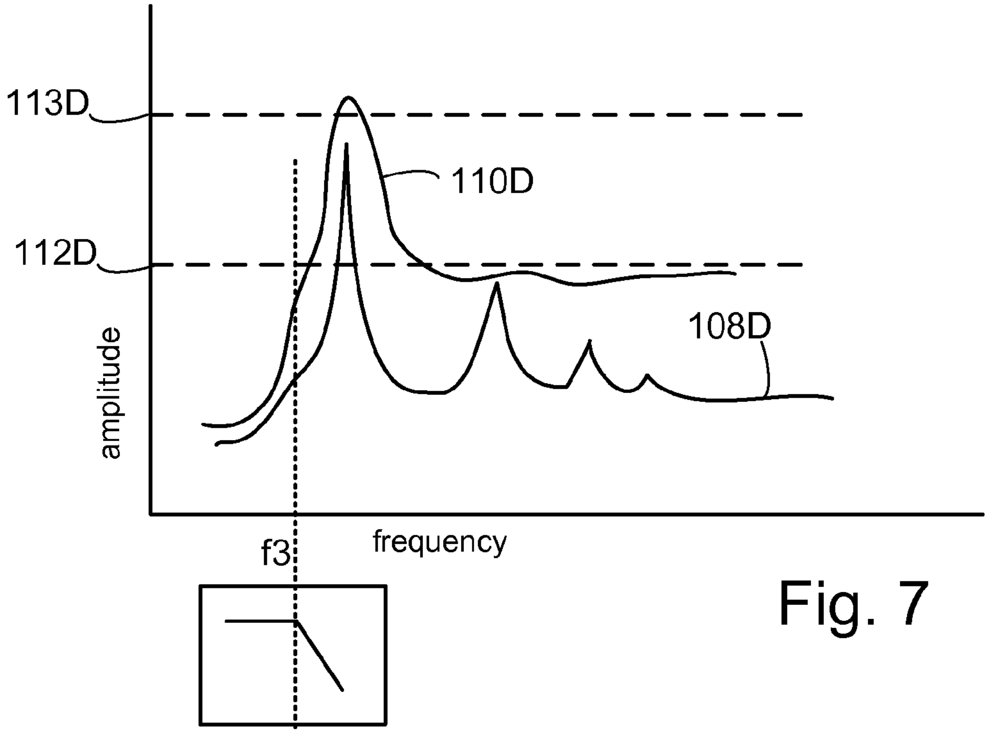
Figure 8:
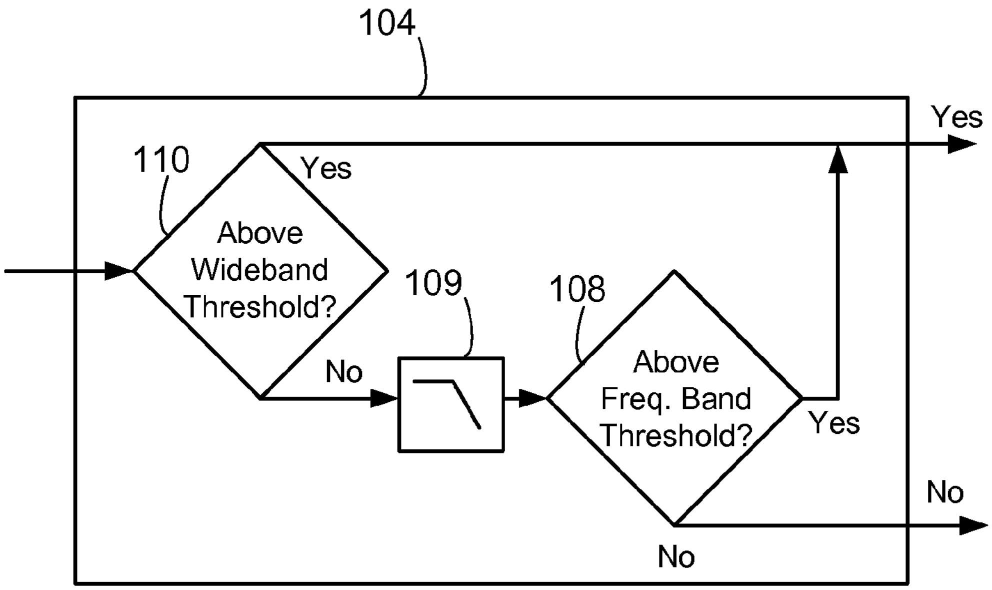
FIG. 8 is a logical block diagram of a portion of the operation of an active noise reduction system.

In the situation of FIG. 6 (as indicated by engine noise curve 108D and interfering noise curve 110D), the presence of high amplitude, interfering noise can be accurately determined by the method shown graphically in FIG. 7 and logically in FIG. 8. The method of FIGS. 7 and 8 includes both the frequency band threshold 112D of FIG. 6 and a broadband threshold 113D. The high noise determination block 104 of FIG. 8 includes the determination methods of both FIG. 3 (block 110) and FIG. 5 (block 108). If either threshold is exceeded, it is determined that high amplitude interfering noise is present. If neither threshold is exceeded, it is determined that high amplitude interfering noise is not present. FIG. 8 shows the effect of the logic of the block 104. There are equivalent processes that yield the same result; for example decision block 110 can precede decision block 108, or the noise signal can be presented to blocks 108 and 110 in parallel, and the outputs of decision block 108 and 110 be processed by an OR operator. Prior to block 108, the noise signal may be lowpass (as indicated by low pass filter 109) or bandpass filtered to facilitate comparison with the threshold.

In one embodiment, the noise signal is filtered with a low pass filter with a break frequency of 20 Hz, a low frequency threshold of 0.1 and a wide band threshold of 0.3 where 1.0 represents a 120 dB SPL signal level. Other embodiments may have different thresholds, with 1.0 representing other signal levels, and the low pass filter may have some other break frequencies.

The high noise determination block of FIGS. 7 and 8 can be expanded to include more than two tests to determine if high amplitude interfering noise is present and different logical arrangements.

Returning to FIG. 2, if it is determined that there are high amplitude interfering noise present, the noise signal is modified at block 106. One method of modifying the noise signal so that the adaptive filter does not diverge is to reduce the gain of the microphone for a period of time, for example, 100 msec. Other methods of modifying the noise signal include band limited attenuation. A consequence of reducing the gain of the microphone is that the adaptive system "coasts", that is it continues to output a cancellation signal, but does not attempt to adapt to cancel the interfering noise.

Numerous uses of and departures from the specific apparatus and techniques disclosed herein may be made without departing from the inventive concepts. Consequently, the invention is to be construed as embracing each and every novel feature and novel combination of features disclosed herein and limited only by the spirit and scope of the appended claims.

What is claimed is:

1. Apparatus comprising:

a feed forward active noise reduction system comprising a vehicle cabin;

a transducer for transducing acoustic noise in the vehicle cabin to a noise signal;

circuitry for determining the amplitude of the noise signal in a limited portion of the frequency range;

circuitry for comparing the amplitude of the noise signal in the limited portion of the frequency range with a limited frequency range threshold, wherein the limited frequency range is one of below the frequency of the first amplitude peak of the engine noise, or between amplitude peaks of engine noise; and circuitry for modifying the noise signal if the amplitude of the noise signal in the limited portion of the frequency range exceeds the limited frequency range threshold.

2. An apparatus according to claim 1, further comprising:

circuitry for determining the amplitude of the noise signal over a broadband frequency range;

circuitry for comparing the amplitude of the noise signal in the broadband frequency range with a broadband threshold; and circuitry for modifying the noise signal if the amplitude of the noise signal in the limited portion of the frequency range exceeds the limited frequency range threshold or the amplitude of the noise signal in the broadband frequency range exceeds the broadband threshold.

3. An apparatus according to claim 2, wherein the broadband frequency range threshold is different than the limited frequency range threshold.

4. An apparatus according to claim 1, wherein the circuitry for modifying the noise signal comprises circuitry for modifying a gain applied to the noise signal.

5. An apparatus according to claim 1, further comprising a low pass filter for filtering the noise signal to provide a low pass filtered noise signal; and circuitry for providing the low pass filtered noise signal to the circuitry for comparing the noise signal in the limited portion of the frequency range.

6. An apparatus according to claim 1, further comprising:

a band pass filter for filtering the noise signal to provide a band pass filtered noise signal; and circuitry for providing the band pass filtered noise signal to the circuitry for comparing the noise signal in the limited portion of the frequency range.

7. Apparatus comprising:

a feed-forward active noise reduction system, comprising a transducer for transducing acoustic noise at a location to a noise signal;

circuitry for determining the amplitude of the noise signal in a broadband frequency range;

circuitry for comparing the amplitude of the noise signal in the broadband frequency range with a broadband threshold;

circuitry for determining the amplitude of the noise signal over a limited portion of the broadband frequency range;

circuitry for comparing the amplitude of the noise signal in the limited portion of the broadband frequency range with a limited frequency range threshold, wherein the limited frequency range is one of below the frequency of the first amplitude peak of the engine noise, or between amplitude peaks of engine noise; and circuitry for modifying the noise signal if the amplitude of the noise signal in the broadband frequency range exceeds the broadband threshold or the amplitude of the noise signal in the limited portion of broadband frequency range exceeds the limited frequency range threshold.

8. An apparatus according to claim 7, wherein the circuitry for modifying the noise signal comprises circuitry for modifying a gain applied to the noise signal.

9. An apparatus according to claim 7, further comprising:

a low pass filter for filtering the noise signal to provide a low pass filtered noise signal; and circuitry for providing the low pass filtered noise signal to the circuitry for comparing the noise signal in the limited portion of the broadband frequency range.

10. An apparatus according to claim 7, further comprising:

a band pass filter for filtering the noise signal to provide a band pass filtered noise signal; and circuitry for providing the band pass filtered noise signal to the circuitry for comparing the noise signal in the limited portion of the broadband frequency range.

11. An apparatus according to claim 7, wherein the active noise reduction system is for reducing acoustic noise in a vehicle cabin.

12. An apparatus according to claim 7, wherein the broadband threshold is different than the limited frequency range threshold.

13. A method for operating a feed forward active noise reduction system, comprising:

transducing acoustic noise in a vehicle cabin to a noise signal;

determining the amplitude of the noise signal in a limited portion of the frequency range;

comparing the amplitude of the noise signal in the limited portion of the frequency range with a limited frequency range threshold, wherein the limited frequency range is one of below the frequency of the first amplitude peak of noise resulting from operation of a vehicle engine, or between amplitude peaks of the noise resulting from the operation of the vehicle engine; and if the amplitude of the noise signal in the limited portion of the frequency range exceeds the limited frequency range threshold, modifying the noise signal.

14. A method according to claim 13, further comprising:
determining the amplitude of the noise signal over a broadband frequency range;
comparing the amplitude of the noise signal in the broadband frequency range with a broadband threshold; and
if the amplitude of the noise signal in the limited portion of the frequency range exceeds the limited frequency range threshold or the amplitude of the noise signal in the broadband frequency range exceeds the broadband threshold, modifying the noise signal.

15. A method according to claim 13, wherein the modifying the noise signal comprises modifying a gain applied to the noise signal.

16. A method according to claim 13, further comprising low pass filtering the noise signal prior to the comparing the noise signal in the limited portion of the frequency range.

17. A method according to claim 13, further comprising band pass filtering the noise signal prior to the comparing the noise signal in the limited portion of the frequency range.

18. The method of claim 13, wherein the modifying prevents the feed-forward active noise reduction system from diverging in the presence of high amplitude noise not resulting from the operation of the engine of the vehicle.

19. The method of claim 13 wherein the method detects the presence of high amplitude noise not resulting from the operation of the engine of the vehicle.

20. A method for operating a feed-forward active noise reduction system, comprising:
detecting acoustic energy at a location;
transducing the acoustic noise to a noise signal;
determining the amplitude of the noise signal in a broadband frequency range;
comparing the amplitude of the noise signal in the broadband frequency range with a broadband threshold;
determining the amplitude of the noise signal over a limited portion of the broadband frequency range;
comparing the amplitude of the noise signal in the limited portion of the broadband frequency range with a limited frequency range, wherein the limited frequency range is one of
below the frequency of a first amplitude peak of noise resulting from the operation of an engine, or
between amplitude peaks of noise resulting from operation of the engine; and
if the amplitude of the noise signal in the broadband frequency range exceeds the broadband threshold or the amplitude of the noise signal in the limited portion of the broadband frequency range exceeds the limited frequency range threshold, modifying the noise signal.

21. A method according to claim 20, wherein the modifying the noise signal comprises modifying a gain applied to the noise signal.

22. A method according to claim 20, further comprising low pass filtering the noise signal prior to the comparing the noise signal in the limited portion of the broadband frequency range.

23. A method according to claim 20, further comprising band pass filtering the noise signal prior to the comparing the noise signal in the limited portion of the broadband frequency range.

24. A method according to claim 20, wherein the location is in a vehicle cabin.

25. A method according to claim 20 wherein the broadband threshold is different than the limited frequency range threshold.

26. The method of claim 20, wherein the modifying prevents the feed-forward active noise reduction system from diverging in the presence of high amplitude noise not resulting from operation of the engine.

27. The method of claim 20, wherein the method detects the presence of high amplitude noise not resulting from the operation of the engine.

* * * * *